United States Patent [19]
Attal et al.

[11] Patent Number: 5,564,951
[45] Date of Patent: Oct. 15, 1996

[54] ELECTRICAL CABLE CONNECTOR AND METHOD OF MAKING

[75] Inventors: Lucien Attal, Anaheim; David L. Swendson, Garden Grove, both of Calif.

[73] Assignee: Baxter International Inc., Deerfield, Ill.

[21] Appl. No.: 200,619

[22] Filed: Feb. 23, 1994

[51] Int. Cl.$^6$ .................................................. H01R 23/02
[52] U.S. Cl. .................. 439/676; 29/858; 29/883; 439/205; 439/271; 439/281; 439/345; 439/680; 439/930
[58] Field of Search .................... 439/344, 496, 439/676, 930, 206, 205, 680, 345, 858; 29/883, 874

[56] References Cited

U.S. PATENT DOCUMENTS

| | | | |
|---|---|---|---|
| 3,065,445 | 11/1962 | Crimmins | 439/496 |
| 3,149,897 | 9/1964 | Martineck | 439/494 |
| 3,258,831 | 7/1966 | Angele et al. | 29/884 |
| 3,696,319 | 10/1972 | Olsson | 439/496 |
| 4,786,259 | 11/1988 | Paul | 439/344 |
| 4,806,117 | 2/1989 | Johnston | 439/344 |
| 4,825,876 | 5/1989 | Beard | 128/675 |
| 5,015,197 | 5/1991 | Redmond et al. | 439/329 |
| 5,048,531 | 9/1991 | Spotts et al. | 128/675 |
| 5,074,039 | 12/1991 | Hillbish et al. | 29/883 |
| 5,135,002 | 8/1992 | Kirchner et al. | 128/672 |
| 5,147,215 | 9/1992 | Pritulsky | 439/344 |
| 5,178,563 | 1/1993 | Reed | 439/676 |
| 5,217,388 | 6/1993 | Brown | 439/455 |

FOREIGN PATENT DOCUMENTS

| | | |
|---|---|---|
| 1440183 | 1/1969 | Germany. |
| 2223126 | 11/1972 | Germany. |
| 2704806 | 8/1978 | Germany. |

*Primary Examiner*—Neil Abrams
*Attorney, Agent, or Firm*—Poms, Smith, Lande & Rose; Bruce M. Canter

[57] ABSTRACT

A disposable blood pressure sensor assembly (10) includes a blood pressure sensor module (12), an electrical cable (18) extending from the blood pressure sensor module (12), and an electrical connector (20) carried on the electrical cable (18). The electrical connector (20) forms a projecting portion (38) having an end surface (58). The electrical cable (18) has a cable jacket (68) which forms an end surface (66). The electrical connector (20) includes a conductor contact portion (60) of each of the electrical conductors (62) of the electrical cable (18), which conductor contact portion (60) is un-insulated and is arrayed and disposed outwardly on the connector (20) for direct electrical contact. Connector end surface (58) and cable jacket end surface (66) cooperatively define the surface across which conductor contact portions (60) extend. The connector (20) and its matching connector (22) include, respectively, a slot (72) and a key (76) for polarization and detents (82) and a pin (80) for connector latching. Also included in connector (20) is an air vent slot (104).

44 Claims, 3 Drawing Sheets

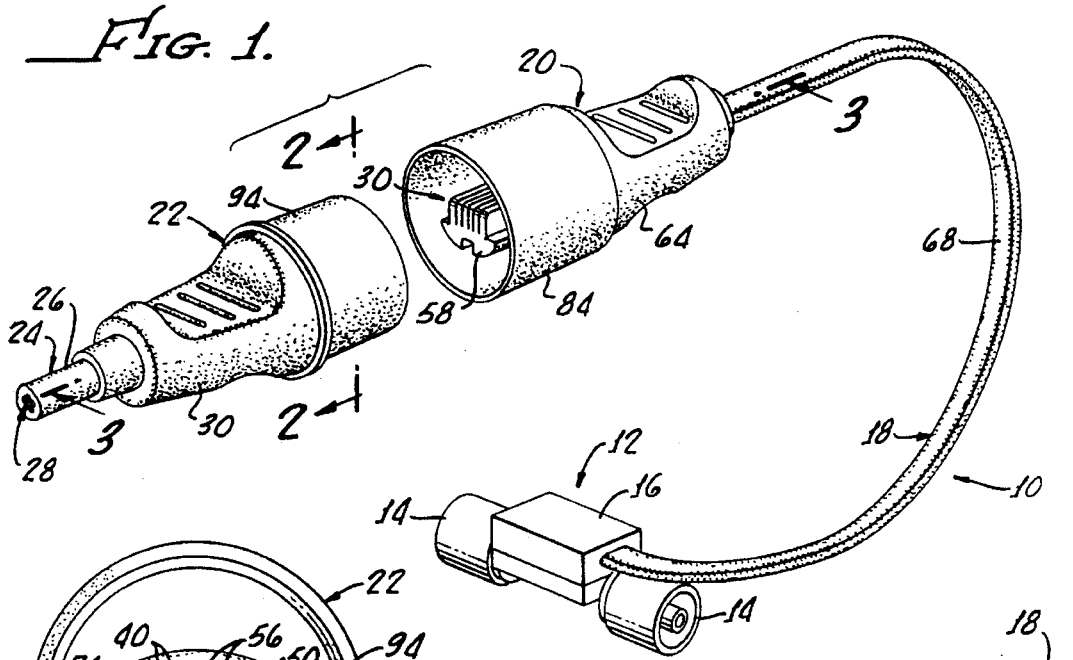
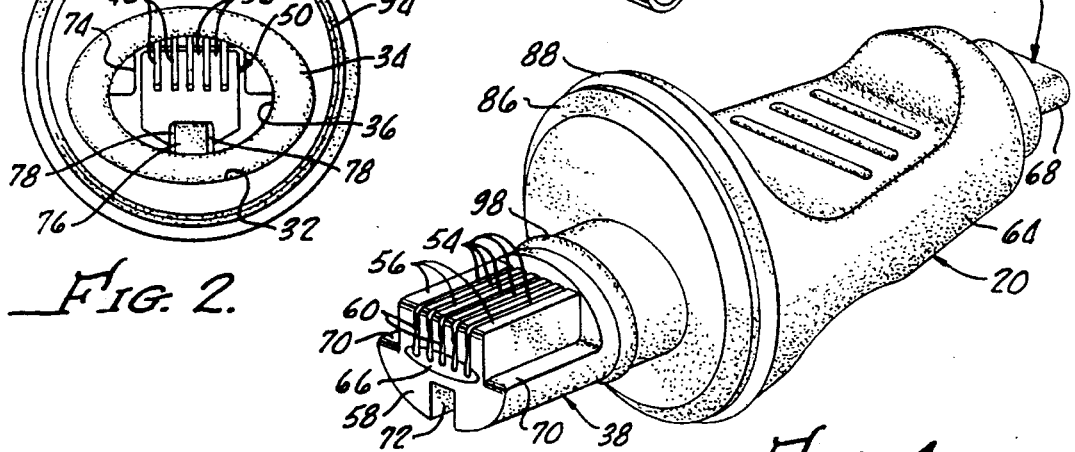
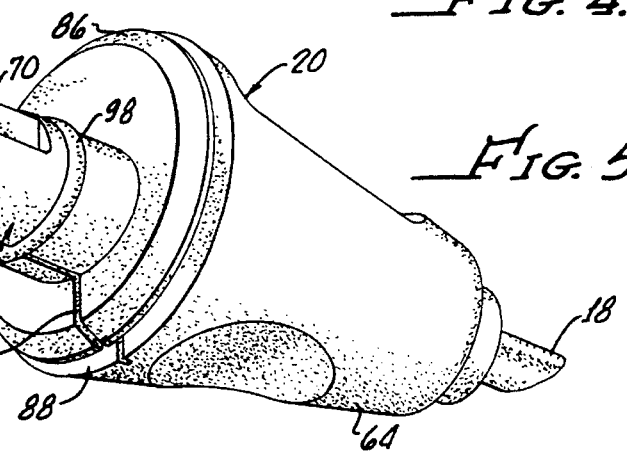
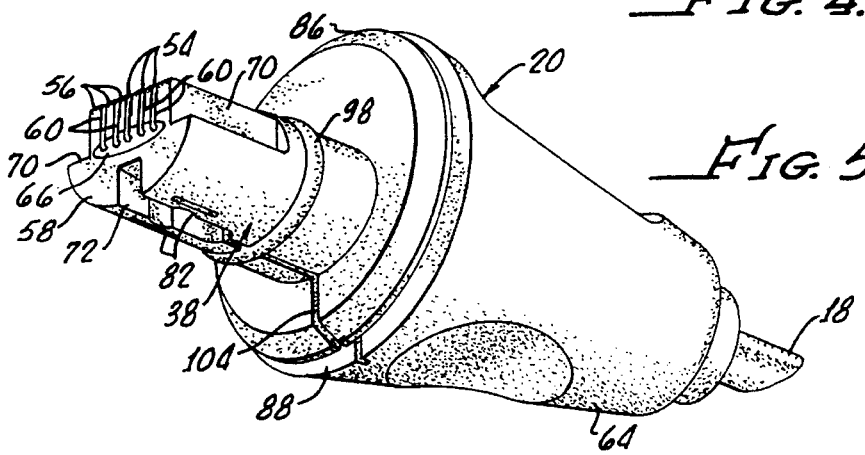

ELECTRICAL CABLE CONNECTOR AND METHOD OF MAKING

BACKGROUND OF THE INVENTION

1. Field of the Invention

The present invention is in the field of connectors for electrically interconnecting electrical conductors of electrical cables, and in the field of method of making such connectors. More particularly, the present invention is in the field of connectors for multi-conductor electrical cables, in which the connector provides for individual connection of each conductor of the multi-conductor electrical cable to a corresponding electrical conductor of another multi-conductor electrical cable, or to other structure.

2. Related Technology

Current technology includes a wide variety of multi-conductor electrical cables, and a similarly wide variety of connectors for such cables. These connectors generally provide for individual connection of the electrical conductors of a cable either to the corresponding conductors of another cable or to other electrical structure. For example, in the home, the common two-conductor or three-conductor electrical extension cord for house-current is well-known. This extension cord includes a male connector plug at one end and a female connector receptacle at the other end.

Another common example of a multi-conductor electrical cable connector is the modular telephone connector presently in wide use. This connector provides for electrically connecting up to five conductors of a telephone cable either to five corresponding conductors of another length of telephone cable, or to corresponding conductors of another structure, such as a telephone. In the case of both the house-current extension cord and the modular telephone connector, the actual electrical interconnection between cables or other structures is effected by mutual contact of pre-formed or stamped metallic contacts carried by a pair of connectors. Frequently, these metallic contacts are formed of a springy and shape-retaining material, such as phosphor-bronze. When the connectors of a pair are engaged with one another, the contacts distort slightly into electrical contact as the male and female components of the connector pair, such as a plug and receptacle, for example, are engaged with one another.

In the process of manufacturing many connectors for multi-conductor electrical cables, the pre-formed contacts are attached by soldering or crimping to individual end portions of each conductor from which the electrical insulation has first been stripped. Subsequently, these contacts are placed into receiving portions of a mold cavity which also has provision for sealingly closing about the adjacent length of cable. This mold cavity defines a void space which is configured to the selected shape of the finished connector. The mold cavity void space may be filled with a thermoplastic insulative material, such as polyvinylchloride, for example, or with a thermoset insulative material, such as natural or synthetic rubber. Injection molding or transfer molding, for example, may be used to fill the mold cavity void space with insulative material. After the insulative material cools or cures, the cable and connector with electrical contacts completely enclosed (in the case of a female connector) or partially embedded in insulative material and outwardly projecting therefrom (in the case of a male connector), is removed from the mold cavity.

As can be appreciated from the above, the conventional cable connectors require the fabrication of plural component parts, and the performance of plural manufacturing steps in order to complete the connector. All of these component parts and plural manufacturing steps add to the overall cost of a conventional cable connector. Also, the multiplicity of parts and manufacturing steps for a conventional cable connector increases the opportunity for variability in the manufacturing process, and for quality control problems and high scrap rates.

A conventional multi-conductor electrical cable and connector is known in accord with U.S. Pat. No. 4,703,989, issued 3 Nov. 1987, to J. R. Price, et al. The electrical connector and cable of the '989 patent are employed to connect a disposable blood pressure monitoring assembly to a durable, or reusable, cable and connector. This latter durable cable and connector are connected to a blood pressure monitoring apparatus. The connector and cable of the disposable blood pressure sensor assembly employs plural individual electrically conductive blade members of the so called, "insulation-displacement" type to penetrate the insulation of the cable into electrical contact with the corresponding electrical conductors. These insulation-displacement blades then provide for electrical connection of the respective conductors of the cable to corresponding contacts of the connector carried on the durable cable extending to the monitor.

With a cable connector according to the '989 patent, all of the deficiencies of conventional cable connectors apply. Further, because the cable, its connector, and a molded housing for the blood pressure sensing unit may be manufactured together in a semi-continuous process, defects in the connectors which render them unusable also require the connected length of cable and molded sensor housing also to be scrapped.

SUMMARY OF THE INVENTION

In view of the deficiencies of conventional cable connectors, it is a primary object for this invention to provide a cable connector in which no added or supplementary pre-formed electrical contact elements are employed.

An object for this invention is to provide a cable connector in which the electrical conductors of the connected cable itself are exposed, formed, positioned and separated from one another, and serve as the contacts for the connector.

A further object is to provide an electrical cable connector in which an end portion of the cable insulation jacket forms a part of the connector, and carries the remainder of the connector.

Yet another object of the present invention is to provide a method of making a cable connector according to the present invention.

These and other objects and advantages of the present invention will be apparent from a reading of the following detailed description of a single exemplary preferred embodiment of the present invention, taken in conjunction with the following drawing Figures, in which the same reference numeral refers to the same feature throughout the drawing Figures, or to features which are analogous in structure or function to one another.

BRIEF DESCRIPTION OF THE DRAWING FIGURES

FIG. 1 provides a perspective view of a disposable pressure sensor module with attached cable and cable connector, the latter in confronting relation with a durable cable connector and cable preparatory to interconnection therewith;

FIG. 2 is an enlarged transverse cross sectional view taken along line 2—2 of FIG. 1;

FIGS. 4 and 5 are respective fragmentary upper quarter and lower quarter perspective views of the cable connector seen in FIGS. 1–3, and having a portion thereof removed for clarity of illustration;

Figure 6:
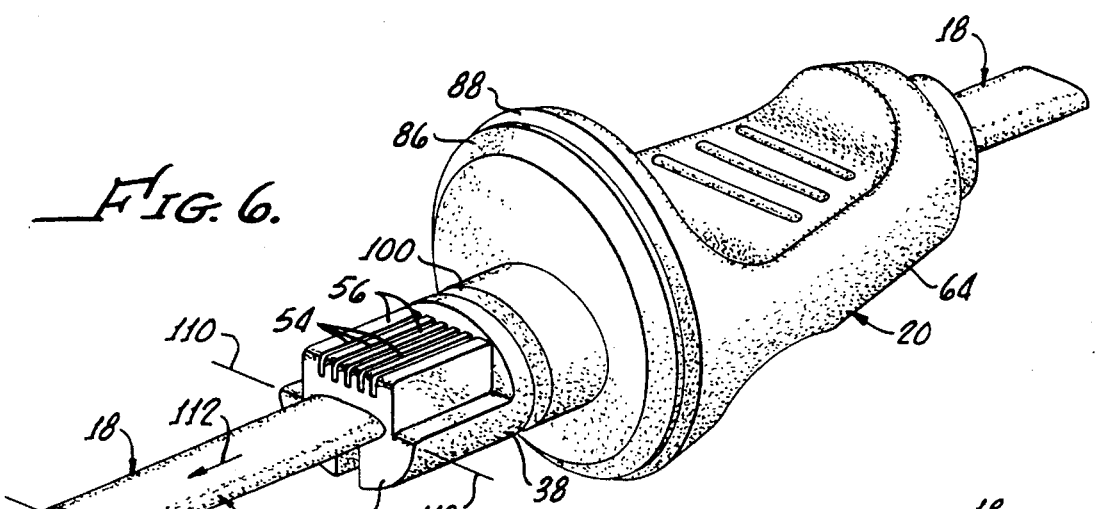
Figure 7:
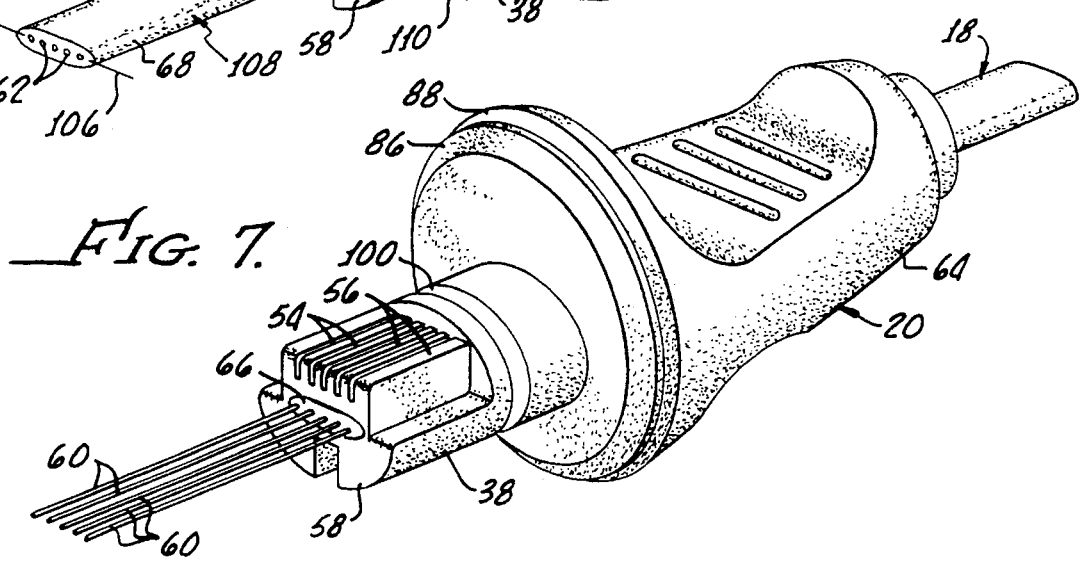
Figure 8:
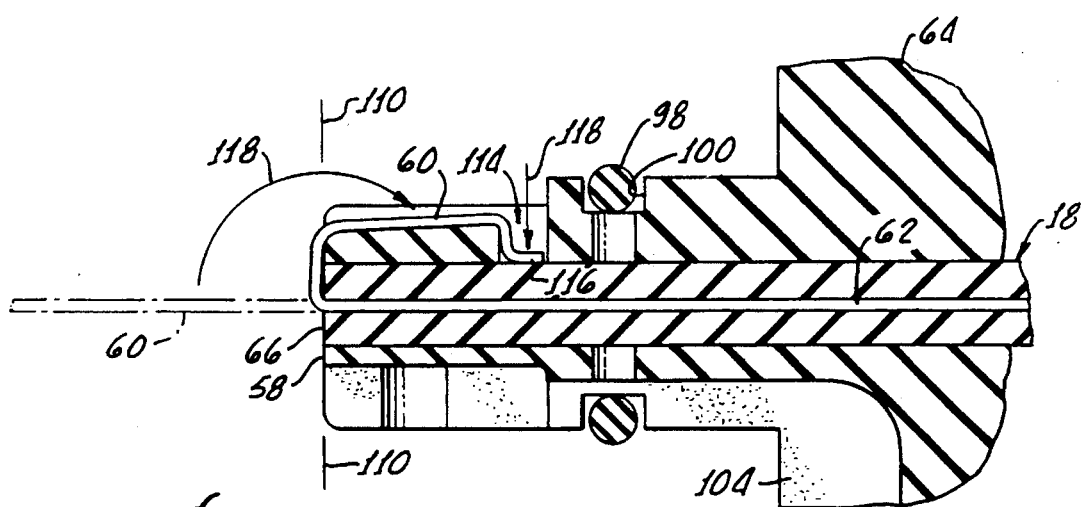

FIGS. 6 and 7 provide fragmentary perspective views of work pieces at successive steps in the processes of making a connector according to the present invention, and FIG. 8 is a fragmentary cross sectional view depicting a step in the process of making a connector according to the present invention, which step is subsequent to the steps and resulting work pieces seen in FIGS. 6 and 7.

DETAILED DESCRIPTION OF AN EXEMPLARY PREFERRED EMBODIMENT OF THE INVENTION

Viewing FIG. 1, a disposable blood pressure sensor assembly 10 includes a sensor module 12, with fluid connection ports at 14. A strain-gauge type of pressure sensor (not shown) is housed within a central case portion 16, and communicates with the ports 14. From the case portion 16 and the strain gauge sensor therein extends a multi-conductor cable 18. The cable 18 extends to, carries, and forms a part of a connector 20, which is to be further described.

Juxtaposed in confronting relationship with the connector 20, is a matching connector 22 carried on a length of cable 24. The cable 24 may be similar to the cable 22 in having the same number of electrical conductors therein, or may be identical with the cable 22. The cable 24 and connector 22 lead to and are electrically attached to a blood pressure monitoring apparatus (not shown). Cable 24 includes an insulating jacket 26, and plural electrical conductors 28. As will be explained, the connectors 20, 22 provide for individual electrical connection of each of the plural electrical conductors 28 to corresponding conductors (identified below) of the cable 18.

Figure 3:
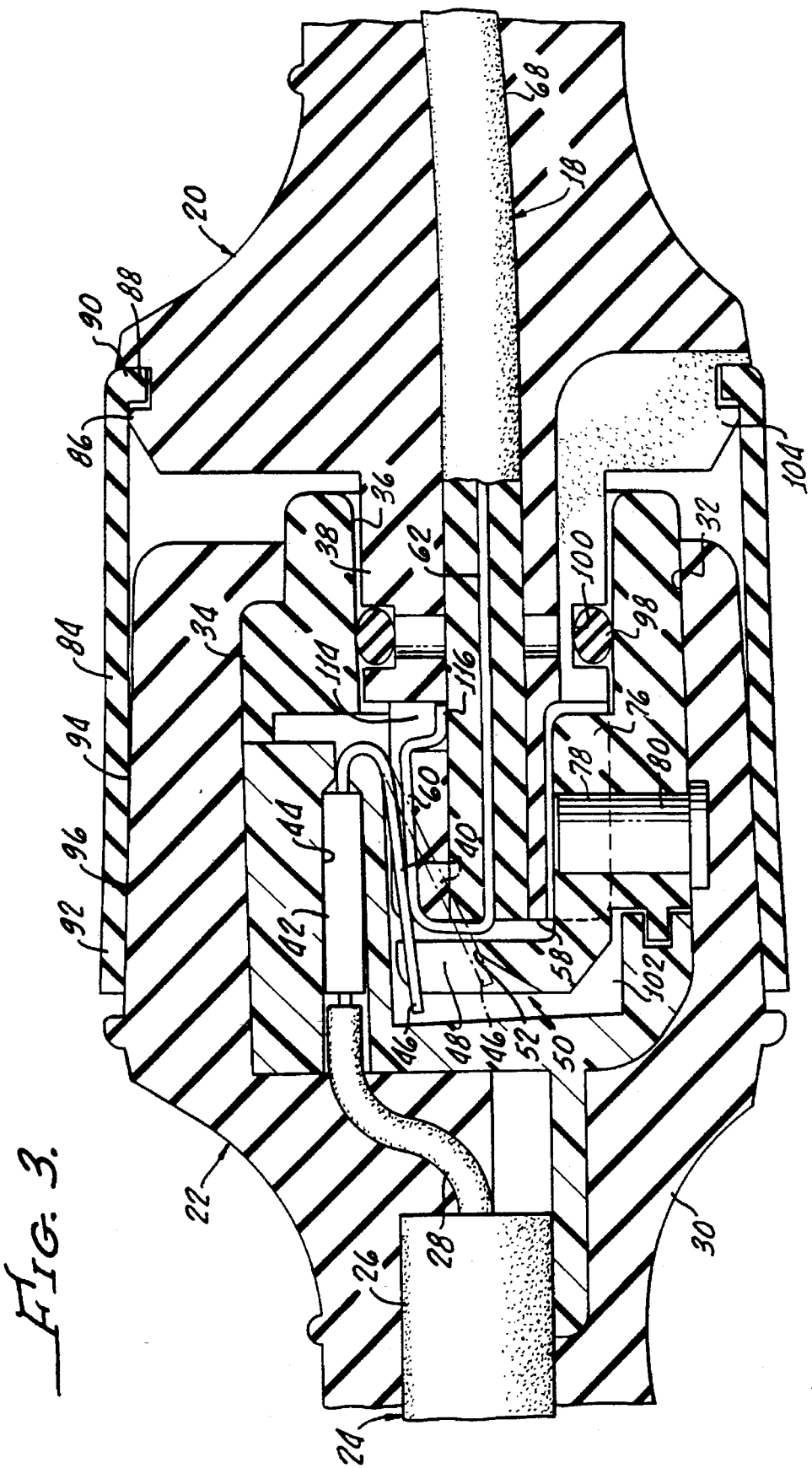
FIG. 3 is an enlarged fragmentary longitudinal cross sectional view taken generally at line 2—2 through the interconnected connectors seen in FIG. 1.

Viewing FIGS. 1 and 3 it is seen that the connectors 20, 22 may be engaged or connected with one another. The connector 22 includes a body 30 of insulative material molded onto the cable 24, and defining a cavity 32 into which a preformed shape-retaining insulative member 34 is received. This pre-formed insulative member 34 defines a cavity 36 which is oval in end view, and into which a shape-matching and axially projecting portion 38 of the connector 20 is received. Within the cavity 36, the connector 22 carries a laterally arrayed plurality of spaced apart resilient wire-like contacts 40. These contacts 40 are each individually carried by a respective connector sleeve 42 which fits within a respective one of a regularly spaced laterally arrayed plurality of bores 44 (only one bore being seen in FIG. 3) defined by the member 34 above the cavity 36 as seen in FIG. 3.

As FIG. 3 shows, a respective one of the plural conductors 28 of the cable 24 is received by each corresponding one of the sleeves 42. Also, the contacts 40 are each individually movable at a free end portion 46 thereof in a respective slot 48 defined by a comb portion 50 of the member 34. As FIG. 3 shows in dashed lines, when the connectors 20, 22 are not connected, the free end portions 46 rest upon a respective shelf feature 52 of the comb 50. When the connectors 20, 22 are connected, the contacts 60 engage the contacts 40, and moves them to the solid line position seen in FIG. 3. The contacts 40 are positioned and movably spaced apart by the cooperation of the comb member 50 and the regular spacing of the plural sleeves 42 in bores 44.

Viewing FIG. 4, it is seen that the projecting portion 38 of connector 20 includes plural elongate slots 54 defined between separating wall portions 56 of the portion 38. These slots 54 open on an end surface 58 of the connector portion 38. The slots 54 are regularly spaced laterally to match the spacing and positioning of the contacts 40 within cavity 36. Returning to consideration of FIG. 3, it is seen that in the solid-line position of the contacts 40, each is received into a corresponding one of the slots 54 and in engagement with a conductor contact portion 60 of plural electrical conductors 62 in and extending outwardly of the cable 18.

FIG. 4 also shows that the connector 20 includes a body 64 of insulative material formed on the cable 18. The body 64 defines the projecting portion 38, and also in part defines the end surface 58. However, a central portion 66 of the end surface 58 is defined by the end of an insulative jacket 68 of the cable 18. As will be further explained, the conductors 62 are stripped of insulation beyond the surface 66 of jacket 68, and are wrapped over this surface 66 and over surface 58 into corresponding ones of the slots 54 between wall portions 58 to define the conductor contact portions 60.

Before proceeding to further describe the process of making the connector 20, it is well to note from FIGS. 1–5, that the connectors 20 and 22 define several cooperative features for purposes of relative positioning (or polarizing), for detenting, for shielding, and for environmental protection of the connectors 20, 22 and contacts 40, 60. For purposes of polarizing the connectors 20, 22, the portion 38 defines a pair of reentrant grooves 70 and a slot 72. The cavity 36 of member 34 is formed with a pair of matching shoulders 74 and a key 76. An end 78 of a pin 80 in the member 34 projects into the cavity 36, interrupts key 76, and forms a cylindrical enlargement on this key. At the slot 72, viewing FIG. 5, the slot 72 is formed with a pair of semi-cylindrical enlargements 82 which receive the end 78 of pin 80 to detent the connectors 20, 22 in engagement with one another when they are engaged to their position seen in FIG. 3.

Shielding of the projecting portion 38 of connector 20, and of the contact portions 60 thereon is provided by a resilient shape-retaining sleeve member 84 which is carried on a matching cylindrical shoulder 86 of the connector 20. At the shoulder 86 the body 64 defines a circumferential groove 88, and the sleeve member 84 defines a collar portion 90 extending radially into the groove 88. A free end portion 92 of the sleeve member 84 defines an inner diameter which is slightly smaller than the outer diameter of a slightly tapered, but generally cylindrical portion 94 of the body 32. Consequently, when the connectors 20, 22 are connected as shown in FIG. 3, the free end portion 92 stretches slightly in diameter over the cylindrical portion 94 to form a moisture-resistant interference fit, indicated with the arrow 96.

In order to provide further environmental protection for the contacts 40, 60, the portion 38 carries an O-ring sealing member 98 in a circumferential groove 100. This O-ring sealing member cooperates with the portion 38 and with member 34 to form a chamber 102 in the cavity 36. The chamber 102 is closed by the sealing member 98 with the exception of a narrow vent slot 104 seen in FIGS. 3 and 5.

This vent slot 104 is necessary to allow the escape of air from the chamber 102 during connection of the connectors 20, 22. If pressurized air were trapped in the chamber 102, it might cause uncoupling of the connectors 20, 22. However, while the narrow vent slot 104 is sufficient to allow the escape of air from chamber 102, it does not adversely effect environmental protection of the contacts 40, 60 because its narrow size causes the surface tension of liquids to prevent entry of these liquids into the cavity 102. Also, because the slot 104 forms the only entrance to the chamber 102, air trapped in this chamber precludes the entry of liquid into the chamber 102, even if the coupled connectors 20, 22 are immersed in liquid, for example.

Returning now to FIGS. 4–8 for a consideration of the process of making the connector 20, and with attention first to FIG. 4, it is seen that the insulative connector body 64 is formed on a length of the cable 18. Preferably, a number of the insulative connector bodies 64 are formed at selectively spaced apart locations on a long length of the cable 18. This formation of the plural connector bodies 64 on the length of cable can be performed in a semi-continuous manufacturing process. The insulative connector bodies 64 are preferably spaced regularly apart on a length of cable 18. The cable length is cut into sections at respective cut lines 106, each spaced from the end surface 58 of the corresponding body 64 so that each cable section has one insulative connector body 64 therein. This location of the cut line 106 results in a length 108 of cable 18 with jacket 68 and conductors 62 extending beyond the surface 58 of portion 38.

At a cut line 110 substantially coextensive with the surface 58, the jacket 68, but not conductors 62, is cut. The cut jacket portion is axially stripped from the conductors 62 (as is indicated by arrow 112), so that projecting conductor contact portions 60 result, viewing FIG. 7. The exposed cut end surface of the jacket 68 forms the central portion 66 of surface 58. At this point a further manufacturing step which is described in connection with FIG. 8 may be performed, or more preferably, one or more intermediate and preparator steps may be performed.

These intermediate and preparatory steps mentioned above involve the provision on the conductor contact portions 60 of a corrosion-resistant coating. Preferably, the conductors 62 are single-strand copper wires. In this case, the conductor contact portions 60 can be plated first with a material, such as nickel, to provide a hard and rigid base for bonding of a top coat of corrosion-resistant material. The corrosion-resistant material is preferably gold or silver. On the other hand, the conductors 62 may be of multi-strand construction, such as a bunch-stranded or a concentric-stranded conductor. For example, the conductors 62 may be of 7-strand (6 around 1) or 19-strand (11 around 7 around 1) concentric-stranded copper wire. In these cases, the multi-strand conductor can be top-coat plated as a group to form the conductor contact portion 60. This top coat plating locks the individual strands of each conductor 62 together with the other strands of this conductor in the stripped and projecting conductor contact portion 60 so that this conductor contact portion 60 acts as a single piece or like a single-strand wire for further forming. After the top coat plating, a corrosion-resistant coating of gold or silver, for example, may also be applied to the contact portions 60.

FIG. 8 shows that the conductor contact portions 60, whether they are single-strand wires or multi-strand wires top-coat plated into a unitary group, are each then bent across the end surfaces 58 and 66, and are further bent back on themselves into a corresponding one of the slots 54, still viewing also FIG. 4. The slots 54 are sized so that the conductor contact portions 60 lead into these slots. Remote from the end surface 58, each slot 54 includes a narrower portion 114 into which an end part 116 of the conductor contact portion 60 is forced in order to captively receive the remainder of the contact portion 60 in slot 54. The remainder of the conductor contact portion 60 is seen to extend generally axially. Folding of the portions 60 into the slots 54 and recesses 114 is shown by arrows 118 in FIG. 8.

An advantage of the present connector 20 resides in comparatively low cost and yet high quality of connector which results from using an end portion of the conductors 62 themselves to form the connector contact portions 60. That is, no additional separate component parts, such as preformed contact members, or insulation-displacement blades, are necessary in order to make the connector 20. Also, the design of the present inventive connector can accommodate virtually any number of plural conductors for electrical interconnection. For example, the presently described connector with fewer slots 54 could be made for cables with fewer than 5 conductors if small size of the connector is important. On the other hand, the width of the connector can be expanded virtually without limit to define a larger number of slots 54 for receiving respective conductor contact portions 60. For example, the connector design of the present invention can easily be expanded to work with many ribbon cables which are presently in use. However, the present connector design is not limited to use with ribbon type cables having plural conductors in a spaced apart flat array. The conductors of a more conventional round cable, for example, could be fanned out in a flat array or in a circular array, for example, while an insulative body, like the body 64, is formed around them. An end portion of these conductors would then define in a flat or circular array, or in an array of chosen geometry, the contact conductor portions for the connector, like the portions 60.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

We claim:

1. An electrical cable and connector comprising:

a length of electrical cable having plural elongate electrical conductors in a parallel flat array, and means for insulating said plural electrical conductors from one another;

a connector body of insulative material carried on said electrical cable near an end thereof;

an exposed conductor contact portion of said plural electrical conductors extending outwardly of said connector body; and said connector body outwardly defining a plurality of parallel slots in a flat array for arraying said conductor contact portions of said plural electrical conductors for direct electrical contact, each of said slots including a respective recess having a portion that is narrower than a respective conductor contact portion for captively receiving an end portion of said respective conductor contact portion.

2. The electrical cable and connector of claim 1 wherein said means for insulating said electrical conductors from one another includes a jacket of insulative material carried upon said plural electrical conductors.

3. The electrical cable and connector of claim 2 wherein said connector body is formed onto said cable jacket, said cable jacket near said end of said cable forming a part of said connector.

4. The electrical cable and connector of claim 3 wherein an end surface of said cable jacket and an end surface of said connector body cooperatively define a surface across which said conductor contact portions of said plural electrical conductors extend.

5. The electrical cable and connector of claim 4 wherein said connector body further defines an axially extending portion defining said end surface of said connector body, and also defining said means for arraying said conductor contact portions.

6. The electrical cable and connector of claim 5 wherein said connector body axially extending portion also carries means for sealingly cooperating with a receptacle for said connector.

7. The electrical cable and connector of claim 6 wherein said means for sealingly cooperating includes an O-ring type seal member.

8. The electrical cable and connector of claim 6 wherein said means for sealingly cooperating includes said connector body also defining means for carrying an axially extending shape-retaining resilient sleeve member, said sleeve member extending axially in congruence with said axially extending body portion.

9. The electrical cable and connector of claim 8 wherein said receptacle further includes a slightly tapering generally cylindrical body portion, said sleeve member stretching slightly over and sealingly engaging said cylindrical body portion upon connection of said connector and said receptacle.

10. The electrical cable and connector of claim 5 wherein said axially extending portion further includes means for detenting said connector in engagement with a receptacle for said connector.

11. The electrical cable and connector of claim 10 wherein said means for detenting includes an elongate keyway extending axially along said axially extending portion, said elongate key including a part-cylindrical enlargement extending generally transversely to said keyway, and said receptacle for said connector including an elongate key receivable into said keyway and having a matching part-cylindrical enlargement for being received into said enlargement of said keyway.

12. A blood pressure sensor assembly comprising:

a blood pressure sensor module for receiving pressurized liquid indicative of a patient's blood pressure level and providing an electrical signal in response thereto;

a multi-conductor electrical cable extending from said blood pressure sensor module for carrying said electrical signal to external blood pressure monitoring apparatus; and a cable connector carried upon said electrical cable adjacent to a free end thereof, wherein the end surface of said electrical cable at said free end and an end surface of said connector body cooperatively define a surface across which conductor contact portions of said plural electrical conductors extend, said cable connector arraying said exposed conductor contact portions of said multiple conductors of said cable across said cooperatively defined surface for direct electrical contact therewith.

13. The blood pressure sensor assembly of claim 12 wherein said electrical cable includes said multiple electrical conductors in a parallel flat array, and a jacket of insulative material carrying said multiple electrical conductors.

14. The blood pressure sensor assembly of claim 13 wherein said cable connector includes a body of insulative material carried upon said jacket, said body of insulative material including a portion with plural longitudinal slots matching in number the number of said plural electrical conductors, and said plural electrical conductors including an exposed portion projecting from an end of said jacket to define said conductor contact portions, said conductor contact portions folding into respective ones of said plural slots for direct electrical contact.

15. The blood pressure sensor assembly of claim 14 wherein said body of insulative material further includes plural wall portions interposing between respective adjacent conductor contact portions.

16. The blood pressure sensor assembly of claim 14 further including a durable electrical cable with a durable connector, the latter defining a cavity for receiving said portion of said body of insulative material with said longitudinal slots and conductor contact portions therein, said connector of said sensor assembly and said durable connector cooperatively defining a chamber in which said conductor contact portions are enclosed, and effecting electrical connection between respective conductors of said electrical cable and said durable electrical cable.

17. The blood pressure sensor of claim 16 also including means for substantially sealingly closing said chamber to prevent entry therein of liquid.

18. The blood pressure sensor of claim 17 wherein said sealing means includes an O-ring type sealing member carried by said portion of said body of insulative material, said sealing member sealingly cooperating with said durable connector.

19. The blood pressure sensor of claim 18 wherein said body of insulative material further carries a tubular sleeve-like resiliently shape-retaining member circumscribing said body portion.

20. The blood pressure sensor of claim 19 wherein said durable connector outwardly defines a generally cylindrical and slightly tapering surface, said sleeve-like member stretching sealingly over said surface upon connection of said connectors to further environmentally protect said conductor contact portions.

21. The blood pressure sensor of claim 16 wherein said connector of said sensor assembly and said durable connector further include means for cooperatively detenting said connectors in connection with one another.

22. The blood pressure sensor of claim 21 wherein said detenting means includes a key defined by one of said connectors with an enlargement along the length of said key, and a slot defined by the other of said connectors for receiving said key and including an enlargement for receiving and retaining the enlargement of the key.

23. The blood pressure sensor of claim 16 wherein said connector of said sensor assembly and said durable connector further include means for cooperatively relatively orienting said connectors for connection together thereof only in a singular relative position.

24. The blood pressure sensor of claim 23 wherein said relative orienting means includes one of said connectors defining a longitudinal groove, and the other of said connectors defining a longitudinal shoulder receivable into said groove.

25. The blood pressure sensor assembly of claim 14 wherein each of said plural longitudinal slots includes a recess having a portion that is narrower than a respective conductor contact portion for captively receiving and end portion of said respective conductor contact portion.

26. A method of providing individual electrical connection with the electrical conductors of a multi-conductor electrical cable, said method comprising the steps of:

providing a connector body on said electrical cable, which connector body provides for arraying said conductors;

providing an end surface of said connector body and an end surface of said electrical cable to cooperatively define a surface across which said conductor contact portions of said plural electrical conductors extend; and outwardly exposing a conductor contact portion of each arrayed electrical conductor across said cooperatively defined surface on said connector body for direct electrical contact therewith.

27. The method of claim 26 further including the step of molding said connector body directly into an insulative jacket of said multi-conductor cable.

28. The method of claim 27 including the steps of stripping an end portion of said insulative jacket from said multi-conductor cable to expose an end portion of said conductors;

employing said exposed end portion of said conductors as said conductor contact portion thereof; and disposing said conductor contact portions of said conductors outwardly upon said connector in spaced apart array.

29. The method of claim 28 further including the step of forming said connector with plural slots separated from one another by an insulative wall portion of said connector body, and disposing a respective one of said conductor contact portions in one of said plural slots for direct electrical contact.

30. The method of claim 27 further including the step of using an end portion of said cable jacket upon which said connector body is molded to define a portion of said connector.

31. A cable connector for multi-conductor electrical cable comprising an insulative connector body, said connector body including means for receiving therein a portion of the electrical conductors of said multi-conductor cable adjacent an end thereof, said connector body further defining a plurality of parallel slots in a flat array for receiving and outwardly arraying an un-insulated conductor contact portion of each of said electrical conductors for direct electrical contact therewith, each of said slots including a respective recess having a portion that is narrower than a respective conductor contact portion for captively receiving an end portion of said respective conductor contact portion.

32. A disposable blood pressure sensor assembly, said assembly including a blood pressure sensor module responsive to blood pressure level to provide an electrical signal indicative thereof, a multi-conductor electrical cable extending from said blood pressure sensor module for carrying said electrical signal to a monitoring apparatus, and an electrical connector carried upon said electrical cable for electrical interface with a matching connector and cable extending to said monitoring apparatus, said electrical connector including a conductor contact portion of each conductor of said multi-conductor cable, wherein an end surface of said electrical cable and an end surface of said connector body cooperatively define a surface across which said conductor contact portions of said plural electrical conductors extend, which conductor contact portion is outwardly exposed on said electrical connector across said cooperatively defined surface for direct electrical contact therewith by said matching connector.

33. An electrical cable and connector comprising:

a length of electrical cable having plural elongate electrical conductors, and means for insulating said plural electrical conductors from one another, said insulating means including a jacket of insulative material carried upon said plural electrical conductors;

a connector body of insulative material formed onto said cable jacket near said end of said electrical cable forming a part of said connector;

an exposed conductor contact portion of said plural electrical conductors extending outwardly of said connector body, wherein an end surface of said cable jacket and an end surface of said connector body cooperatively define the surface across which said conductor contact portions of said plural electrical conductors extend; and said connector body outwardly defining means for arraying said conductor contact portions of said plural electrical conductors across said cooperatively defined surface for direct electrical contact.

34. The electrical cable and connector of claim 33 wherein said connector body further defines an axially extending portion defining said end surface of said connector body, and also defining said means for arraying said conductor contact portions.

35. The electrical cable and connector of claim 34 wherein said connector body axially extending portion also carries means for sealingly cooperating with a receptacle for said connector.

36. The electrical cable and connector of claim 35 wherein said means for sealingly cooperating includes an O-ring type seal member.

37. The electrical cable and connector of claim 35 wherein said means for sealingly cooperating includes said connector body also defining means for carrying an axially extending shape-retaining resilient sleeve member, said sleeve member extending axially in congruence with said axially extending body portion.

38. The electrical cable and connector of claim 37 wherein said receptacle further includes a slightly tapering generally cylindrical body portion, said sleeve member stretching slightly over and sealingly engaging said cylindrical body portion upon connection of said connector and said receptacle.

39. The electrical cable and connector of claim 34 wherein said axially extending portion further includes means for detenting said connector in engagement with a receptacle for said connector.

40. The electrical cable and connector of claim 39 wherein said means for detenting includes an elongate keyway extending axially along said axially extending portion, said elongate key including a part-cylindrical enlargement extending generally transversely to said keyway, and said receptacle for said connector including an elongate key receivable into said keyway and having a matching part-cylindrical enlargement for being received into said enlargement of said keyway.

41. A blood pressure sensor assembly comprising:

a blood pressure sensor module for receiving pressurized liquid indicative of a patient's blood pressure level and providing an electrical signal in response thereto;

a multi-conductor electrical cable extending from said blood pressure sensor module for carrying said electrical signal to external blood pressure monitoring apparatus, said cable including multiple electrical conductors in a parallel flat array, and a jacket of insulative material carrying said multiple electrical conductors;

a cable connector carried upon said electrical cable adjacent to a free end thereof, said cable connector including a body of insulative material carried upon said cable jacket, said body of insulative material including a portion with plural longitudinal slots matching in number the number of said plural electrical conductors, and said plural electrical conductors including an exposed portion projecting from an end of said cable jacket to define said conductor contact portions, and said conductor contact portions folding into respective ones of said plural slots for direct electrical contact, said body of insulative material including plural wall portions interposing between respective adjacent conductor contact portions;

a durable electrical cable with a durable connector, the latter defining a cavity for receiving said portion of said body of insulative material with said longitudinal slots and conductor contact portions therein, said connector of said sensor assembly and said durable connector cooperatively defining a chamber in which said conductor contact portions are enclosed, and effecting electrical connection between respective conductors of said electrical cable and said durable electrical cable; and means for substantially sealingly closing said chamber to prevent entry therein of liquid, including an O-ring type sealing member carried by said portion of said body of insulative material, said sealing member sealingly cooperating with said durable connector.

42. The blood pressure sensor of claim 41 wherein said body of insulative material further carries a tubular sleeve-like resiliently shape-retaining member circumscribing said body portion.

43. The blood pressure sensor of claim 42 wherein said durable connector outwardly defines a generally cylindrical and slightly tapering surface, said sleeve-like member stretching sealingly over said surface upon connection of said connectors to further environmentally protect said conductor contact portions.

44. A blood pressure sensor assembly comprising:

a blood pressure sensor module for receiving pressurized liquid indicative of a patient's blood pressure level and providing an electrical signal in response thereto;

a multi-conductor electrical cable extending from said blood pressure sensor module for carrying said electrical signal to external blood pressure monitoring apparatus, said cable including multiple electrical conductors in a parallel flat array, and a jacket of insulative material carrying said multiple electrical conductors;

a cable connector carried upon said electrical cable adjacent to a free end thereof, said cable connector including a body of insulative material carried upon said cable jacket, said body of insulative material including a portion with plural longitudinal slots matching in number the number of said plural electrical conductors, and said plural electrical conductors including an exposed portion projecting from an end of said cable jacket to define said conductor contact portions, and said conductor contact portions folding into respective ones of said plural slots for direct electrical contact, said body of insulative material including plural wall portions interposing between respective adjacent conductor contact portions;

a durable electrical cable with a durable connector, the latter defining a cavity for receiving said portion of said body of insulative material with said longitudinal slots and conductor contact portions therein, said connector of said sensor assembly and said durable connector cooperatively defining a chamber in which said conductor contact portions are enclosed, and effecting electrical connection between respective conductors of said electrical cable and said durable electrical cable;

said connector of said sensor assembly and said durable connector further including means for cooperatively detenting said connectors in connection with one another, said detenting means including a key defined by one of said connectors with an enlargement along the length of said key, and a slot defined by the other of said connectors for receiving said key and including an enlargement for receiving and retaining the enlargement of the key.

\* \* \* \* \*